(12) United States Patent
Gau

(10) Patent No.: US 8,591,817 B1
(45) Date of Patent: Nov. 26, 2013

(54) ELEVATED TEMPERATURE ASSAY SYSTEM

(75) Inventor: Jen-Jr Gau, Pasadena, CA (US)

(73) Assignee: GeneFluidics, Inc., Irwindale, CA (US)

( * ) Notice: Subject to any disclaimer, the term of this patent is extended or adjusted under 35 U.S.C. 154(b) by 2216 days.

(21) Appl. No.: 10/702,412

(22) Filed: Nov. 5, 2003

Related U.S. Application Data

(60) Provisional application No. 60/428,567, filed on Nov. 21, 2002.

(51) Int. Cl.
*G01N 27/00* (2006.01)
(52) U.S. Cl.
USPC ....... 422/82.01; 435/7.1; 435/287.1; 204/193
(58) Field of Classification Search
None
See application file for complete search history.

(56) References Cited

U.S. PATENT DOCUMENTS

| | | | | |
|---|---|---|---|---|
| 4,702,808 | A | * | 10/1987 | Lemelson ................. 204/157.41 |
| 5,004,913 | A | * | 4/1991 | Kleinerman .............. 250/227.21 |
| 5,087,122 | A | * | 2/1992 | Ostrander et al. ........... 356/73.1 |
| 5,131,941 | A | * | 7/1992 | Lemelson .................... 75/10.19 |
| 5,147,611 | A | * | 9/1992 | Stout et al. ....................... 422/78 |
| 5,498,392 | A | * | 3/1996 | Wilding et al. .............. 422/68.1 |
| 5,653,939 | A | * | 8/1997 | Hollis et al. ..................... 422/50 |
| 6,391,558 | B1 | * | 5/2002 | Henkens et al. .................. 435/6 |

OTHER PUBLICATIONS

Affymetrix product bulletin, GeneChip® Instrument Systems, hybridization oven.

Anderson, et al., "A miniature integrated device for automated multistep genetic assays", Nucleic Acids Research, 2000, vol. 28, No. 12.

Krishnam, et al., "A novel strategy for the design of multiple reaction systems for genetic analysis" Sensors and Actuators A 95 (2002) pp. 250-258.

Locascio, et al., "Integrated Silicon Microheating Elements using Silicon-on-Plastic Drop-In Functionality", Analytical Chemistry Division and Semiconductor Electronics Division National Institute of Standards & Technology, Gaithersburg, MD 20899 Proceeding µTAS 2000 Conference, Twente, The Netherlands, May 14-18, 2000.

Mao, et al., "Reusable Platforms for High-Throughput On-Chip Temperature Gradient Assays" Anal. Chem.2002, 74,5071-5075.

McMillan, et al., "Application of advanced microfluidics and rapid PCR to analysis of microbial targets" *Proceedings of the 8th International Symposium on Microbial Ecology, Microbial Ecology in Industry*, 1999.

McMillan, William A., "Real-time point-of-care molecular detection of infectious disease agents", American Clinical Laboratory p. 29-31.

Yu, et al., "A Miniaturized and Integrated Plastic Thermal Chemical Reactor for Genetic Analysis", Microfluidics Laboratory, Motorola Labs, Department of Electrical Engineering and Computer Science, University of Michigan, Ann Arbor, Motorola BioChip Systems.

\* cited by examiner

*Primary Examiner* — Paul Hyun
(74) *Attorney, Agent, or Firm* — Gavrilovich, Dodd & Lindsey, LLP

(57) ABSTRACT

The assay system includes at least one thermally responsive medium positioned so as to transfer thermal energy to a solution constrained in a solution constraining region. The assay system further includes a beam distribution system configured to distribute an energy beam to a thermally responsive medium. The thermally responsive medium interacts with the energy beam so as to elevate the temperature of the thermally responsive medium.

28 Claims, 8 Drawing Sheets

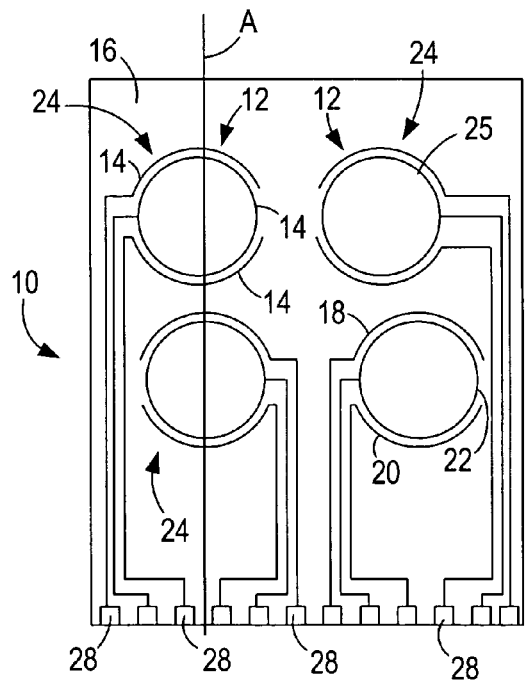
Figure 1A
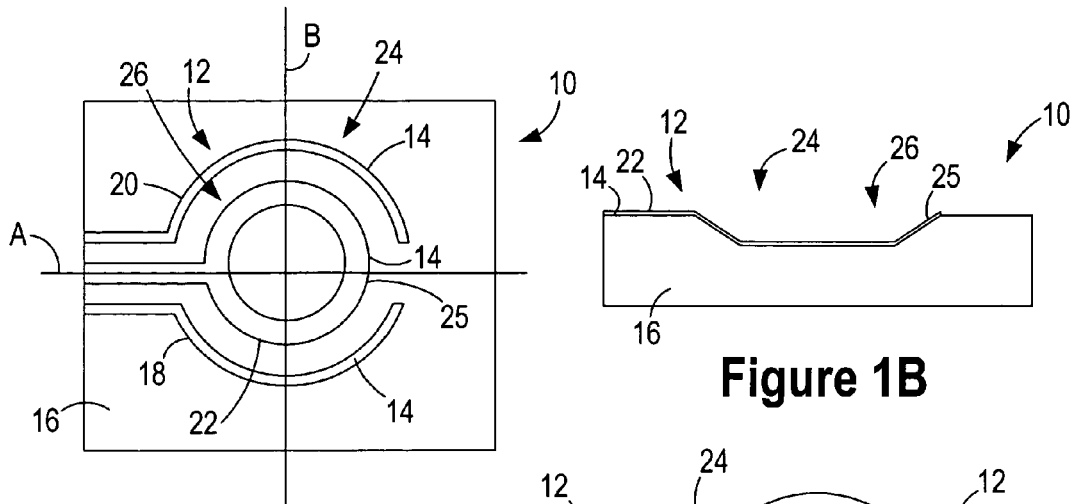
Figure 1B
Figure 1C
Figure 1D

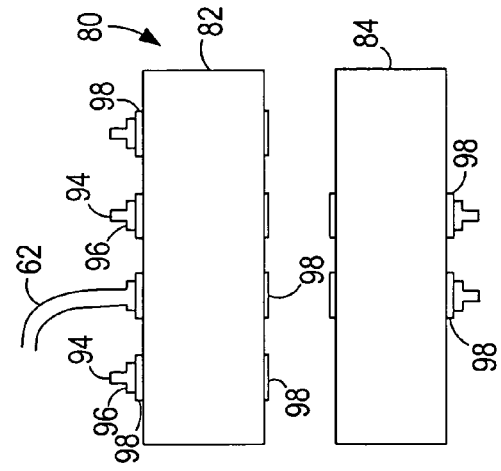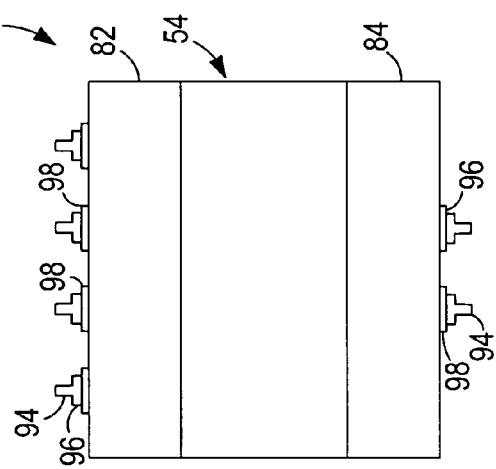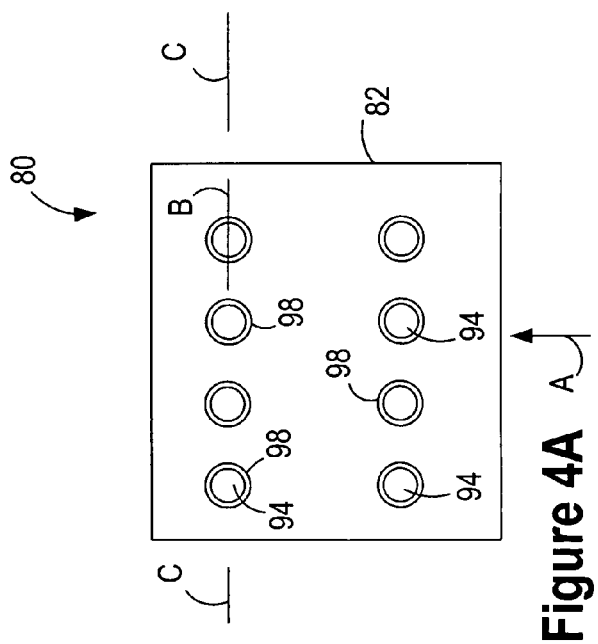

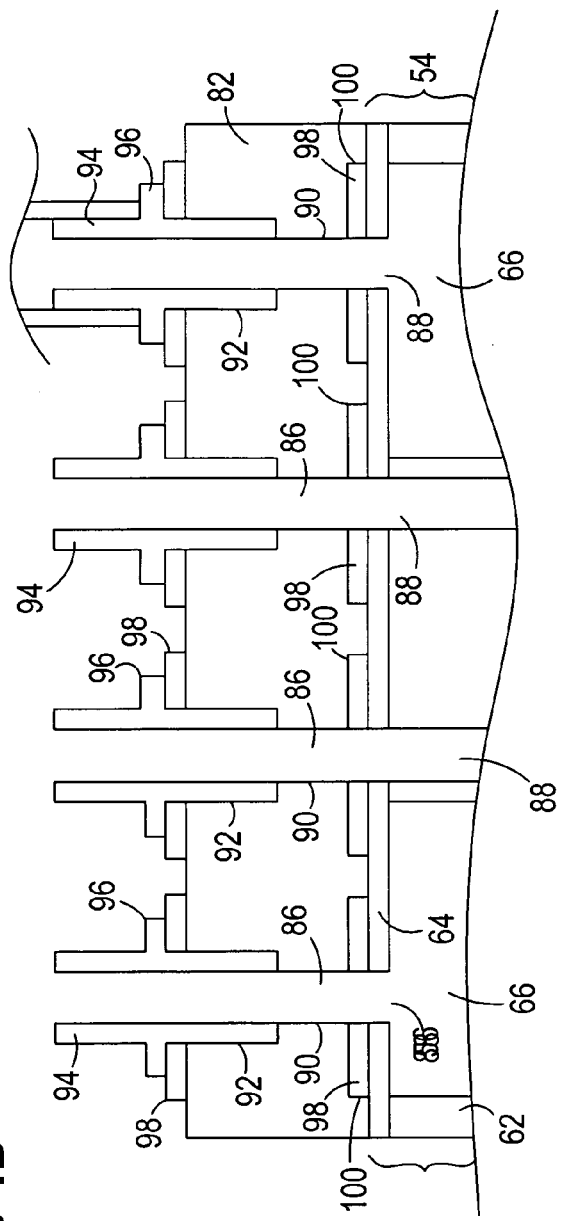
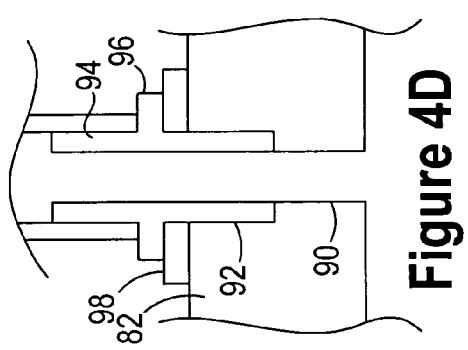

ELEVATED TEMPERATURE ASSAY SYSTEM

RELATED APPLICATIONS

This application claims priority to U.S. Provisional Application Ser. No. 60/428,567, filed on Nov. 21, 2002, entitled "Elevated Temperature Assay System" and incorporated herein in its entirety.

BACKGROUND

1. Field of the Invention

The invention relates to assays and more particularly to equipment for use with assays.

2. Background of the Invention

A variety of assays have been developed to detect the presence of biological agents in a sample. The desire for assays that can be performed in the field has increased the demand for smaller and more efficient assay equipment. This demand has been met with equipment that employs one or more sensors mounted on a chip or a wafer.

An assay includes one or more procedures during the preparation of a sample for analysis and during the actual analysis of the sample. Some of the procedures are often most effective when performed at elevated temperatures. When the assay is being performed in conjunction with chip mounted sensors, these procedures often require that one or more solutions be placed on a sensor. As a result, there is a need for an assay system that allows solutions positioned on a sensor to be used at elevated temperatures.

SUMMARY OF THE INVENTION

The invention relates to an assay system. The assay system includes at least one thermally responsive medium positioned so as to transfer thermal energy to a solution constrained in a solution constraining region. The assay system further includes a beam distribution system configured to distribute an energy beam to a thermally responsive medium. The thermally responsive medium interacts with the energy beam so as to elevate the temperature of the thermally responsive medium.

One or more of the solution constraining regions can be positioned in a cartridge. In some instances, the solution constraining region is a reservoir in the cartridge. One or more of the solution constraining regions can be positioned on an assay chip having one or more sensors configured to detect an agent. In some instances, at least a portion of each sensor serves as a solution constraining region. In some instances, at least one of the solution constraining regions on the assay chip is spaced apart from each of the sensors.

One embodiment of the assay system includes one or more sensors for detection of an agent. The assay system also includes an energy beam source configured to produce an energy beam. The energy beam interacts with at least a portion of a sensor so as to elevate the temperature of the sensor. The assay system also includes a beam distribution system. The beam distribution system distributes the energy beam to the one or more sensors. The energy beam can be a light beam and the energy beam source can be a laser.

In some instances, the one or more sensors are a plurality of sensors and the beam distribution system is configured to direct the beam from one of the sensors to another. In other instances, the beam distribution system is configured to split the beam into a plurality of energy beam portions that are each directed to a sensor. In other instances, the beam distribution system includes a plurality of energy beam sources that are each configured to produce a beam directed to at least one sensor.

The assay system can include one or more lenses positioned along a path of the energy beam and configured to adjust a spot size of the energy beam on the one or more sensors.

The assay system can also include an attenuator configured to at least partially attenuate the power of the energy beam. In some instances, the attenuator is configured to be moved in and out of a path of the energy beam.

Another embodiment of the assay system includes one or more solution constraining mechanisms for constraining a solution to a solution constraining region. The system also includes electronics configured to monitor one or more electrical characteristics of a circuit. The circuit is configured such that at least one electrical characteristic of the circuit change in response to changes in the temperature of a solution constrained to the solution constraining region. In some instances, the solution constraining region is configured to constrain the solution adjacent to a sensor for detection of an agent.

The electronics can also be configured to elevate the temperature of a sensor in response to the one or more electrical characteristics indicating that the temperature of the associated sensor falls below a first target temperature. The electronics can be configured to elevate the temperature of the associated sensor by directing at least a portion of an energy beam to the associated sensor.

The electronics can also be configured to reduce the temperature of a sensor in response to the one or more electrical characteristics indicating that the temperature of the associated sensor is elevated above a second target temperature. The electronics can be configured to reduce the temperature of the associated sensor by reducing the power of an energy beam directed to that sensor. In some instances reducing the power of the energy beam directed to that sensor includes disrupting delivery of the energy beam to that sensor.

The one or more sensors can be configured to be removed from assay equipment configured to perform the assay. The assay equipment can include a frame that incorporates the beam distribution system. In some instances, the one or more sensors are located on an assay chip that is configured to be removed from the assay equipment. The one or more sensors can also be located in a cartridge that is configured to be extracted from the assay equipment.

The invention also relates to a method of performing an assay. The method includes directing an energy beam to a thermally responsive medium positioned so as to transfer thermal energy to a solution constrained in a solution constraining region. The energy beam interacts with the thermally responsive medium so as to elevate the temperature of the thermally responsive medium. In some instances, the solution constraining region is configured to constrain the solution adjacent to a sensor for detection of an agent.

Another embodiment of a method of operating an assay includes monitoring one or more electrical characteristics of a circuit. The circuit is configured such that at least one electrical characteristic of the circuit changes in response to changes in the temperature of a solution constrained to the solution constraining region. The method also includes adjusting a temperature of a thermally responsive medium in response to the one or more electrical characteristics of the associated circuit. The thermally responsive medium is configured to transfer thermal energy to the solution in the solution constraining region.

BRIEF DESCRIPTION OF THE FIGURES

FIG. 1A is a topview of an assay chip having a plurality of sensors. Each sensor is configured to detect the presence of an agent.

FIG. 1B is a cross section of the chip shown in FIG. 1A taken at the line labeled A.

FIG. 1C is a cross section of the chip shown in FIG. 1A taken at the line labeled B.

FIG. 1D is a topview of an assay chip having a plurality of sensors.

FIG. 3A is a topview of the cartridge. The cartridge includes a reservoir where a solution can be stored. At a later time, the solution can be transported from the reservoir to a sensor on the assay chip. The reservoir is positioned over the assay chip.

FIG. 3B is a sideview of the cartridge illustrated in FIG. 3A taken in the direction of the line labeled A.

FIG. 3C is a cross section of the cartridge illustrated in FIG. 3A taken along the line labeled B.

FIG. 4A is a topview of an interface system configured to be employed with a cartridge constructed according to FIG. 3A. The interface system provides an interface between the cartridge and an assay system.

FIG. 4B is a sideview of the interface system illustrated in FIG. 4A looking in the direction of the arrow labeled A. The interface system includes a first interface member and a second interface member.

FIG. 4C is a sideview of a cartridge positioned between the first interface member and the second interface member.

FIG. 4D is a cross section of the interface member seen in FIG. 4A taken along the line labeled B.

FIG. 4E is a cross section of the interface member illustrated in FIG. 4A taken between the lines labeled C. The interface member of FIG. 4E is shown coupled with the cartridge of FIG. 3A.

DETAILED DESCRIPTION OF THE PREFERRED EMBODIMENT

Figure 2A:
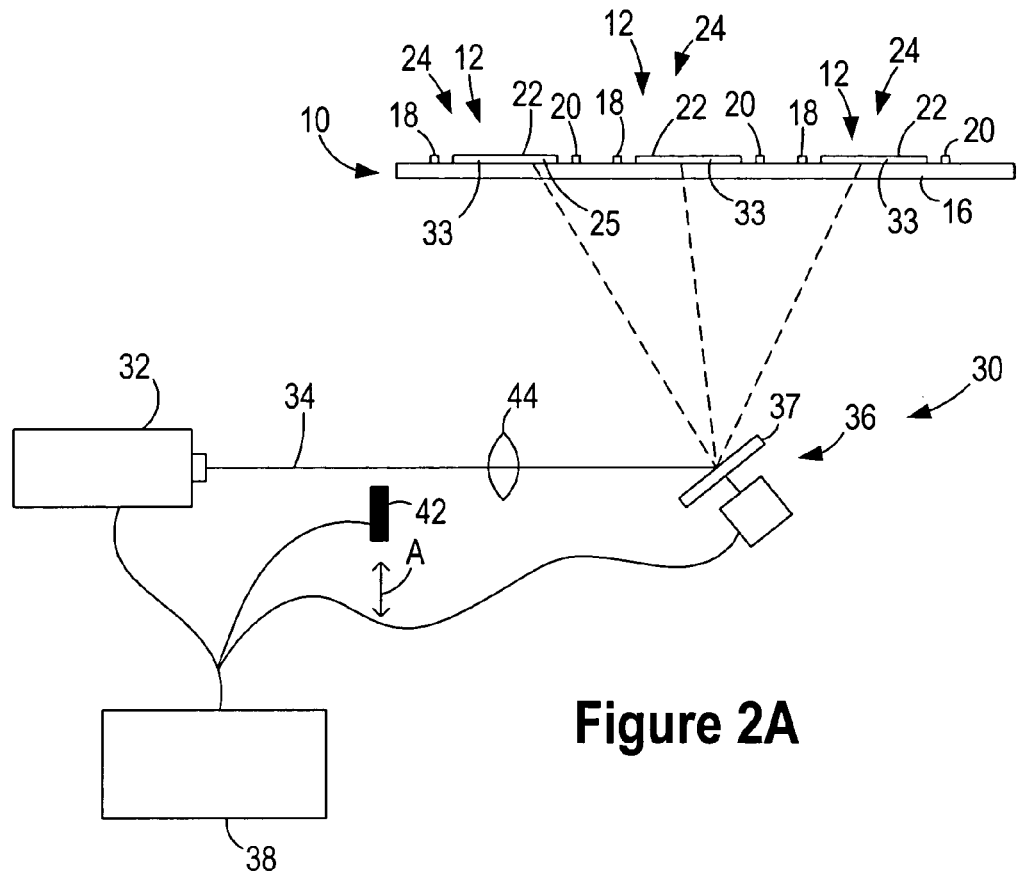
FIG. 2A illustrates a temperature control system for controlling the temperature of one or more sensors. The temperature control system includes a beam distribution system configured to steer an energy beam to each of the sensors.

The invention relates to an assay system. The assay system includes one or more sensors for detection of an agent such as a chemical agent or a biological agent. The assay system also includes a beam distribution system for distributing an energy beam to the sensors or to the periphery of the sensors. The interaction of the energy beam with a sensor causes the temperature of the sensor to rise. As a result, the assay system allows the temperature of the sensors to be elevated.

The assay system can control the duration of the energy beam at each of the sensors. In some instances, the duration of the energy beam on different sensors is different. Sensors that receive the energy beam for different periods of time are elevated to different temperatures. As a result, the assay system can maintain different sensors at different temperatures independently.

The assay system can also include a temperature feedback control system that allows the temperature of a particular one of the sensors to be adjusted in response to the temperature of that sensor. The temperature feedback control system can be employed to maintain each sensor above a target temperature or within a desired temperature range.

During operation of a sensor, one or more solutions are delivered onto the sensor. Heat transfer between the sensor and the solution causes the temperature of the solution to rise to about the temperature of the sensor. As a result, the assay system allows the solutions to be used at elevated temperatures. The ability to use these solutions at elevated temperatures can improve the performance of the procedures employed during preparation of a sample for analysis and during the actual analysis.

FIG. 1A through FIG. 1C illustrate an example of a portion of an assay chip 10 having a sensor 12 for the detection of an agent. FIG. 1A is a topview of the chip 10 and FIG. 1B is a cross section of the chip 10 shown in FIG. 1A taken at the line labeled A. FIG. 1C is a cross section of the chip 10 shown in FIG. 1A taken at the line labeled B.

The chip 10 includes a plurality of electrodes 14 positioned on a substrate 16. Although the substrate 16 is shown as being constructed from a single material, the substrate 16 can have a composite construction. The electrodes 14 include a reference electrode 18 and a counter electrode 20 positioned adjacent to a working electrode 22. The working electrode 22 can be constructed of a metal such as gold. Other suitable materials for the electrodes 14 include, but are not limited to, silver, copper, platinum, chromium, aluminum, titanium and nickel.

The chip 10 includes a solution constraining mechanism 25 configured to constrain a solution to a solution constraining region 24. For instance, FIG. 1C illustrates a solution positioned on the working electrode 22. Surface tension causes the solution to be constrained on the working electrode. Accordingly, the working electrode can serve as the solution constraining mechanism and a surface of the working electrode serves as the solution constraining region 24. In some instances, the drop also extends over the reference electrode 18 and the counter electrode 20. Surface tension can cause the solution to be constrained in place over the working electrode 22, the reference electrode 18 and the counter electrode 20. As a result, the reference electrode 18 and the counter electrode 20 serve in conjunction as the solution constraining mechanism 25.

The sensor 12 can employ other structures to help constrain a solution to a solution constraining region 24. For instance, the sensor 12 can optionally include a well 26. The working electrode 22 can cover the bottom and sides of the well 26 or only a portion of the well 26. Alternatively, the working electrode 22 can extend from inside the well 26 to outside the well 26. The well 26 is optional and the sensor 12 can be flat.

In some instances, the substrate 16 can serve as a solution constraining mechanism. For instance, the substrate 16 can have a hydrophobic surface positioned so as to constrain the solution on the sensor. For instance, at least the portion of the substrate 16 adjacent to the electrodes 14 can be constructed of a hydrophobic medium such as a plastic. Alternatively, at least the portion of the substrate 16 adjacent to the electrodes can have a hydrophobic coating. The hydrophobic nature of the surface drives the solution off the surface and onto the electrodes 14 and accordingly helps constrain the solution on the electrodes. The hydrophobic surface of the substrate 16 is optional and the surface of the substrate need not be hydrophobic.

In some instances, one or more of the electrodes 14 have a hydrophilic surface that serves as a solution constraining mechanism. The working electrode, the reference electrode and/or the counter electrode can have a hydrophilic surface. For instance, a working electrode constructed of gold can have a hydrophilic coating such as a protein coating. Each electrode 14 having a hydrophilic surface has an increased affinity for the solution. As a result, the hydrophilic nature of the electrode 14 draws the solution onto the electrodes 14 and accordingly helps constrain the solution on the electrodes 14. The surface of the electrodes need not be hydrophilic.

Examples of solutions to be positioned on the sensor 12 include, but are not limited to, solutions employed during the preparation of a sample to be analyzed and can be the sample itself. In some instances, a solution constrained on the solution constraining region 24 is washed off the sensor 12 at a later step in the operation of the sensor. As a result, one or more solutions can be temporarily positioned on the sensor 12 during the preparation of the sample to be analyzed.

Although FIG. 1A and FIG. 1B illustrate the chip 10 as having a single sensor 12, a chip 10 can include a plurality of sensors 12 as illustrated in FIG. 1D. The sensors 12 can be arranged in an array on the chip 10. Each of the sensors 12 includes a working electrode 22, a reference electrode 18 and a counter electrode 20. The working electrode 22, reference electrode 18 and counter electrode 20 are each in electrical communication with a pad 28 positioned at a side of the chip 10. Although each of the pads 28 is shown as being positioned along the same side of the chip 10, the pads 28 can be positioned on different sides of the chip 10.

During operation of an assay chip 10 to analyze a sample, the chip 10 is in electrical communication with electronics (not shown) configured to apply a potential between the working electrode 22 and the reference electrode 18 of a sensor 12 while monitoring current passing through a circuit that includes the working electrode 22, a solution positioned on the sensor 12 and the counter electrode 20. The sensor can be employed as an electrochemical sensor. For instance, when analyzing a sample, the potential applied between the working electrode 22 and the reference electrode 18 is raised to a level that can cause electron transfer to occur between the working electrode 22 and a component in the sample. The electron transfer allows current to flow through the circuit that includes the working electrode 22, the sample and the counter electrode 20. As a result, a current flowing through the working electrode 22 and the counter electrode 20 indicates that the component is present in the sample while the lack of current indicates that the component is not present in the sample. In other instances, a constant current or controlled known current is forced into the working electrode and the potential change at the working electrode is monitored to determine the quantity of the component in the sample. In some instances, the assay is configured such that the presence of the component in the sample indicates the presence of a second component in the sample. The second component is often the component being sought by the assay.

Operation of the sensor so as to detect the presence of an agent is discussed in more detail in U.S. patent application Ser. No. 09/848,727, filed on May 3, 2001, entitled "Biological Identification System with integrated Sensor Chip" and incorporated herein in its entirety.

As noted above, it is often desirable to keep one or more solutions positioned on the sensor 12 at an elevated temperature during the sample preparation or during the analysis of the sample. FIG. 2A illustrates a temperature control system 30 configured to elevate the temperature of a solution positioned on a sensor 12. The temperature control system 30 includes a beam source 32 configured to produce an energy beam 34. A suitable beam 34 includes, but is not limited to, a light beam. Further, a suitable beam source 32 includes, but is not limited to, a laser.

FIG. 2A also shows a cross section of an assay chip 10. The illustrated cross section is similar to a cross section of the assay chip 10 shown in FIG. 1D taken along the line labeled A for an assay chip 10 having nine sensors 12. Each sensor includes a thermally responsive medium 33. The temperature of a thermally responsive medium 33 elevates upon interaction of the thermally responsive medium 33 with the energy beam 34. For instance, when the energy beam 34 is a laser, a suitable thermally responsive medium 33 includes, but is not limited to, a metal such as gold. When the laser is incident on gold, the temperature of the gold increases. The thermally responsive medium 33 is positioned to transfer thermal energy to a solution positioned in the solution constraining region 24 of a sensor 12. As a result, employing the energy beam to increase the temperature of the thermally responsive medium 33 increases the temperature of a solution positioned in the solution constraining region 24.

In some instances, the working electrode 22 is a thermally responsive medium 33. The working electrode 22 is a suitable region of the sensor 12 because a solution positioned in the solution constraining region 24 of the sensor is positioned adjacent to the working electrode 22 as shown in FIG. 1C. Hence, there is a high degree of thermal energy transfer between the working electrode 22 and a solution in the solution constraining region 24. As a result, the temperature of the working electrode 22 can serve as a reasonable approximation of the temperature of a solution on the working electrode 22.

A suitable material for the working electrode 22 is a metal such as gold. Gold has a relatively high thermal conductivity. The high thermal conductivity will allow thermal energy to quickly diffuse through the working electrode 22 and can result in a more even distribution of heat. The quick diffusion of thermal energy reduces the tendency of the working electrode 22 to generate a hot spot. As a result, the beam 34 can be incident on the working electrode 22 without generating a hot spot on the working electrode 22.

The temperature control system 30 also includes a beam distribution system 36 for distributing the beam to the sensors. The beam distribution system 36 includes a steering mirror 37 configured to steer the beam 34. A suitable steering mirror 37 is the model Digital Micromirror Device (DMD), manufactured by Texas Instruments, located in Dallas, Tex.

The temperature control system 30 also includes electronics 38 in communication with the steering mirror 37 and the beam source 32. The electronics can include one or more processors. Suitable processors include, but are not limited to, programmed general purpose digital computers, microprocessors, digital signal processors (DSP), integrated circuits, application specific integrated circuits (ASICs), logic gate arrays and switching arrays. The electronics 38 can also include one or more machine readable media for storing instructions to be executed by the processor and/or for storing information to be used by the processor while executing instructions. Suitable machine readable media include, but are not limited to, RAM, electronic read-only memory (e.g., ROM, EPROM, or EEPROM), or transmission media such as digital and/or analog communication links.

The electronics 38 are configured to control the operation of the beam source 32. For instance, the electronics 38 can control the power of the beam 34 and/or turn the beam source 32 on or off. Further, the electronics 38 are configured to control the steering mirror 37. As a result, the electronics 38 control the direction in which the beam 34 is steered.

The electronics 38 can employ the steering mirror 37 to steer the beam 34 such that the beam 34 is incident on one or more of the thermally responsive media 33 of a sensor. In some instances, the electronics 38 directs the beam 34 to the working electrode 22 of a sensor to elevate the temperature of the sensor 12. FIG. 2A shows the beam steered so as to be incident on the working electrodes of the sensors 12 on the assay chip 10. The electronics can additionally employ the steering mirror to direct the beam from one sensor to another sensor. For instance, the dashed lines in FIG. 2A illustrate that the electronics 38 can steer the beam 34 so as to be incident on the working electrode of each illustrated sensor 12. Accordingly, the electronics 38 can scan the beam 34 across a selection of sensors. Although FIG. 2A shows the beam 34 scanned over sensors 12 arranged in a line, the steering mirror 37 can also be configured to scan the beam 34 over sensors arranged in a plane. As a result, the beam 34 can be directed to each of the sensors 12 on the assay chip 10 of FIG. 1D. As an alternative to scanning the beam 34 across a plurality of sensors, the electronics 38 can direct the beam 34 to a single sensor.

As will be described in more detail below, the energy beam 34 can be directed to regions of the assay system other than sensors. Accordingly, the energy beam can be scanned over thermally responsive media that are not configured to transfer thermal energy to a sensor. In some instances, the energy beam can be scanned over only thermally responsive media that are not configured to transfer thermal energy to a sensor.

In some instances, the duration of the beam 34 on a particular sensor is determined by the electronics 38. The electronics 38 can increase or decrease the power of the beam delivered to a particular sensor. Suitable methods for changing the beam power at a particular sensor include, but are not limited to, changing the power at the beam source or by employing a beam attenuator as will be discussed below. Reducing the power of the beam directed to a sensor can include disrupting the delivery of the beam 34 to the particular sensor. The delivery of the beam can be disrupted by directing the beam 34 to another thermally responsive medium 33, by turning off the beam source 32 or by employing a beam attenuator that provides complete blocking of the beam.

In the embodiment illustrated in FIG. 2A, the beam 34 passes through the substrate 16 of the assay chip 10. The substrate 16 can be selected so as to be substantially transparent to the beam 34. For instance, when the beam 34 is a light beam 34, the substrate 16 can be selected so as to be transparent to the light beam 34. Clear plastic, glass and clear synthetic polymer are examples of suitable substrate materials that are transparent to the light beam 34. When the substrate 16 is substantially transparent to the beam 34, the beam 34 experiences a low level of attenuation when passing through the substrate. As an alternative to selecting the material of the substrate 16 to be transparent to the beam 34, the temperature control system 30 can be arranged so the beam 34 does not pass through the substrate 16 before being incident on a thermally responsive medium 33. For instance, the beam 34 can be incident on the sensor 12 from a position above the sensor 12 with or without passing through material positioned around the sensor 12.

During operation of the temperature control system, the electronics 38 scan the beam 34 across each of the sensors that are to have an elevated temperature. The scan can be conducted such that each of the sensors has about the same temperature or has a different temperature. Additionally, the duration of the beam 34 on each sensor can be different or can be the same. When the duration of the beam 34 on each sensor is the same, the electronics 38 can operate the beam source 32 such that the power of the beam 34 is adjusted for different sensors. In some instances, the electronics 38 adjust the power of the beam 34 such that the power delivered to at least one sensor is different from the power delivered to other sensors. As a result, the temperature control system 30 allows the sensors 12 to be maintained at different temperatures or at the same temperature.

When the power of the beam 34 is about the same for each thermally sensor, the electronics 38 can operate the beam source 32 so as to adjust the duration of the beam 34 on each sensor. In some instances, the electronics 38 adjust the power of the beam 34 such that duration on at least one sensor 12 is different from the duration on other sensors. As a result, the temperature control system 30 allows the sensors to be maintained at different temperatures or at the same temperature.

Although the above discussion discloses adjusting the power of the beam 34 or the duration of the beam 34, the electronics 38 can be configured to adjust both the power of the beam 34 and the duration of the beam 34. The sequence in which the sensors 12 are scanned can be the same with each scan of the sensors 12. In some instances, the sequence in which the sensors 12 are scanned is not the same with each scan of the sensors 12.

In some instances, it is desired to disrupt delivery of the beam 34. For instance, delivery of the beam 34 to the sensors 12 can be disrupted when each of the sensors is at the desired temperature. The electronics 38 can turn the beam source 32 off to disrupt delivery of the beam 34 to the sensors. As an alternative to turning off the beam source 32, the electronics 38 can optionally be in communication with an attenuator 42 such as a shutter.

The electronics 38 can operate the attenuator 42 so as to disrupt the delivery of the beam 34. For instance, the electronics 38 can move the attenuator 42 in and out of the beam 34 path as illustrated by the arrow labeled A. The attenuator 42 can be configured to provide complete blocking of the beam 34 when in the path of the beam 34. In some instances, the attenuator 42 can provide only partial blocking of the beam 34 when in the path of the beam 34. For instance, the attenuator 42 can include a film that that allows partial transmission of the beam 34. As a result, the attenuator 42 can be employed to reduce the power of the beam 34.

The temperature control system 30 can optionally include one or more lenses 44 configured to be positioned in the path of the beam 34. The one or more lenses 44 can be configured to adjust the spot size of the beam 34 on a thermally responsive medium 33. The one or more lenses 44 can be configured to decrease the spot size of the beam 34 at a thermally responsive medium 33 below the spot size of the beam 34 at the thermally responsive media 33 when the one or more lenses 44 are not employed. Alternatively, the one or more lenses 44 can be configured to increase the spot size of the beam 34 at the thermally responsive media 33 above the spot size of the beam 34 at the thermally responsive media 33 when the one or more lenses 44 are not employed. As a result, the spot size of the beam 34 on the medium can be selected. In some instances, the spot size of the beam 34 is selected so as to be about the same size as the working electrode 22. Accordingly, the energy of the beam 34 is distributed across the working electrode 22. Distributing the beam 34 across the working electrode 22 reduces formation of hot spots on the working electrode 22. In some instances, the position of the one or more lenses 44 along the beam 34 is adjustable. As a result, the spot size can be adjustable.

Figure 2B:
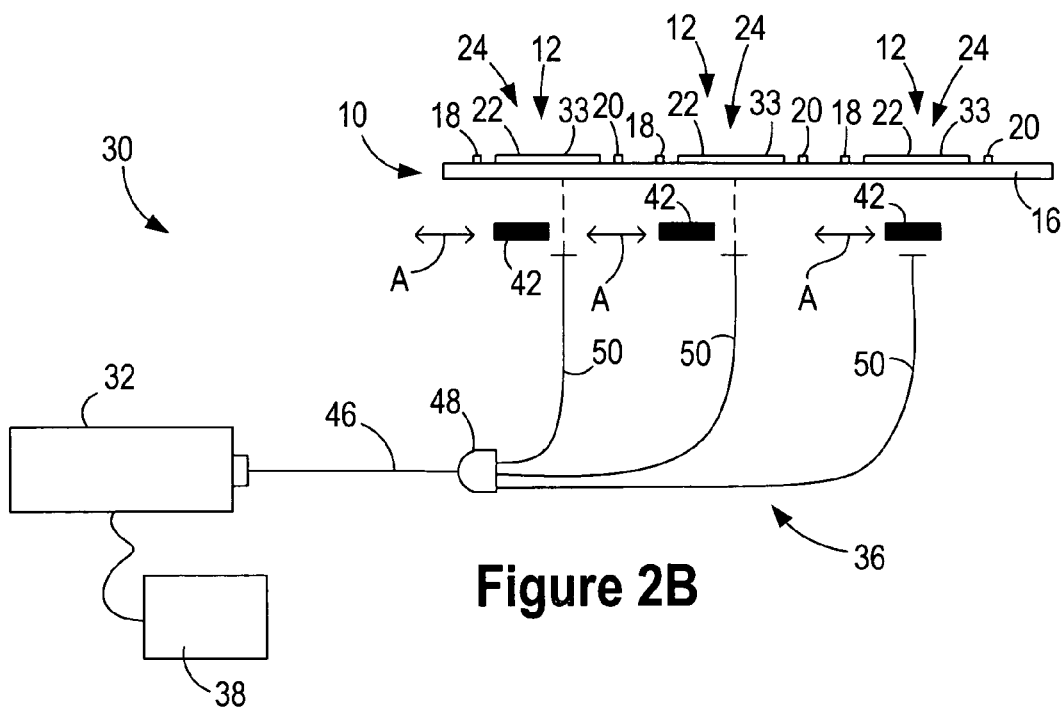
FIG. 2B illustrates a temperature control system for controlling the temperature of one or more sensors. The temperature control system includes a beam distribution system configured to divide an energy beam into a plurality of energy beam portions that are each directed at a sensor.

FIG. 2B illustrates another embodiment of a temperature control system 30. The beam distribution system 36 includes a primary beam guide 46 configured to receive the beam 34 from the beam source 32. A splitter 48 connects the primary beam guide 46 to a plurality of secondary beam guides 50. The beam 34 is propagated along the primary beam guide 46 and the secondary beam guides 50. For instance, when the beam source 32 is a laser, the beam guide 46 can be a waveguide such as an optical fiber. The splitter 48 is configured to distribute a portion of the beam 34 traveling along the primary beam guide 46 to each of the secondary beam guides 50. The secondary beam guides 50 are each arranged such that a beam 34 exiting from a secondary beam guide 50 is directed to a thermally responsive medium 33 so as to elevate the temperature of at least a portion of the thermally responsive medium 33. For instance, the dashed lines in FIG. 2B show the secondary beam guides 50 arranged such that a beam 34 exiting from a secondary beam guide 50 is directed to a sensor 12 so as to elevate the temperature of at least a portion of the sensor 12. Accordingly, each beam portion serves as an energy beam for elevating the temperature of a sensor. Although FIG. 2B shows the secondary beam guides 50 directing the beam portions to sensors 12 arranged in a line, the secondary beam guides 50 can be configured to direct the beam portions to sensors 12 arranged in a plane. As a result, the beam 34 can be directed to each of the sensors 12 on the assay chip 10 of FIG. 1D.

As will be described in more detail below, the energy beam 34 can be directed to regions of the assay system other than sensors. Accordingly, the beam portions can also be directed to thermally responsive media that are not configured to transfer thermal energy to a sensor. In some instances, the beam portions are each directed to responsive media that are not configured to transfer thermal energy to a sensor.

During operation of the energy temperature control system 30, the beam 34 is propagated along the primary beam guide 46 to the splitter 48. The splitter 48 distributes a portion of the beam 34 to each of the secondary beam guides 50. A portion of the beam 34 is propagated along each of the secondary beam guides 50. Each beam portion exits from a secondary beam guide 50 and travels toward the thermally responsive medium 33 of a sensor.

The electronics 38 can be in communication with a plurality of attenuators 42. The electronics 38 can operate the attenuators 42 so as to disrupt the delivery of the beam portion associated with a particular sensor 12. For instance, the electronics 38 can move each attenuator 42 in and out of the path of a beam portion as illustrated by the arrows labeled A. The attenuator 42 can be configured to provide complete blocking of the beam portion when in the path of the beam portion. In some instances, the attenuator 42 can provide only partial blocking of the beam portion when in the path of the beam 34. As a result, the attenuator 42 can be employed to reduce the power of the beam portion delivered to a particular sensor.

The electronics 38 can control the attenuators 42 so as to control the temperature of each sensor 12. For instance, the electronics 38 can move an attenuator 42 out of the path of a beam portion when it is desired to elevate the temperature of the associated sensor 12. Additionally, the electronics 38 can move the attenuator 42 into the path of a beam portion when it is desired to lower the temperature of the associated sensor or when the associated sensor has reached a desired temperature range. Because an attenuator 42 is associated with each sensor 12, different sensors 12 can be maintained at different temperatures.

Although not illustrated, the temperature control system 30 of FIG. 2B can optionally include one or more lenses 44 configured to be positioned in the path of the beam portion. The one or more lenses 44 can be configured to adjust the spot size of the beam portion on the associated thermally responsive medium 33. The one or more lenses 44 allow the spot size of the beam portion at the thermally responsive medium 33 to be selected.

Other mechanisms are available for splitting the beam into beam portions directed to the thermally responsive media 33. For instance, the function of the primary beam guide and the secondary beam guides illustrated in FIG. 2B can be provided with a system of beam splitters configured to split the beam into beam portions and mirrors arranged so as to direct the beam portions to the thermally responsive media 33. Alternatively, the beam distribution system 36 can include a plurality of beam sources 32 in communication with the electronics 38. The beam 34 from each beam source 32 can be aimed at or directed to a particular thermally responsive medium 33. The electronics 38 can turn a beam source 32 off and on to control the temperature of the thermally responsive medium 33 receiving the beam 34 from that beam source 32. As an alternative to turning each beam source 32 on and off, the electronics 38 can be in communication with a plurality of attenuators 42 that are each configured to attenuate a beam 34. The attenuators 42 can be operated as described with respect to FIG. 2B in order to control the temperature of the thermally responsive media 33. Additionally, one or more lenses 44 can be positioned in the path of each beam 34 in order to control the spot size of the beam 34 at the thermally responsive media 33.

Although the above disclosure teaches directing the energy beam 34 to the working electrode of the sensor 12, the energy beam 34 can be directed to other regions of a sensor 12 such as the reference electrode 18 or the counter electrode 20. Additionally, the sensor 12 can include a thermally responsive media 33 that is not operated as an electrode. For instance, a sensor 12 can include a metal pad (not shown) positioned between the working electrode 22 and the reference electrode 18, between the counter electrode 20 and the working electrode 22 or between the reference electrode 18 and the counter electrode 20. The energy beam 34 can be directed to the pad to elevate the temperature of a solution positioned in the solution constraining region 24 of a sensor 12. Accordingly, the temperature of the solution can be elevated without directing the energy beam to one of the electrodes.

Although the above disclosure teaches operating the temperature control system so as to elevate the temperature of a solution positioned in the solution constraining region 24 of a sensor, the temperature control systems of FIG. 2A and FIG.

Figure 2C:
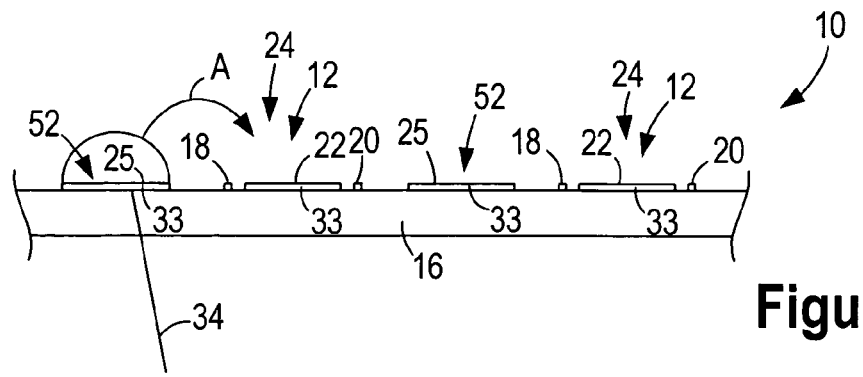
FIG. 2C illustrates a portion of a temperature control system for controlling the temperature of one or more solution constraining regions where a solution is positioned before being transported a sensor.

2B can be operated so as to elevate the temperature of solutions positioned on solution constraining regions 24 that are not part of a sensor. As shown in FIG. 2C, the energy beam 34 or energy beam portion can be directed to a thermally responsive medium 33 that is not included in a sensor 12. FIG. 2C is a cross section of an assay chip 10 having a plurality of secondary solution constraining regions 24. The secondary solution constraining regions 24 are spaced apart from the sensors 12. A thermally responsive medium 33 is positioned to transfer thermal energy to a solution positioned in a secondary solution constraining region 52. The thermally responsive medium 33 can be constructed so as to serve as both a solution constraining mechanism 25 and a secondary solution constraining region 52. For instance, the thermally responsive medium 33 can be constructed such that the surface tension of a solution constrains the solution on a surface of the thermally responsive medium 33. The secondary solution constraining region 52 can include one or more other solution constraining mechanisms for constraining the solution to the secondary solution constraining region 52. The temperature control system can be operated so as to maintain a solution on a secondary solution constraining region 52 at an elevated temperature. The solution can be transported from a secondary solution constraining region 52 to one or more sensors 12 as illustrated by the arrow labeled A.

In some instances, the temperature control system can also be operated so as to maintain the solution at an elevated temperature after the solution has been transported to the sensor 12. For instance, the temperature control system can be configured to direct the energy beam to the sensor after the solution has been transported to the sensor 12. Alternatively, the temperature control system is not operated so as to maintain the solution transported to a sensor 12 at an elevated temperature after the solution is transported to the sensor 12. In some instances, the electrodes 14 of a sensor 12 may have coatings on them that are sensitive to the energy beam 34. As a result, in some instances, it is not desirable to direct the energy beam 34 to the electrodes of the sensor 12. The secondary solution constraining region 52 allows the solution to be transported to the sensor 12 at an elevated temperature without the energy beam being directed to the electrodes.

The electronics 38 can be configured to operate the temperature control systems 30 described above so as to maintain the temperature of one or more sensors 12 at a particular temperature or within a particular temperature range. For instance, the conductivity of a working electrode 22 changes as the temperature of the working electrode 22 changes. The change in conductivity causes the electrical characteristics of a circuit that includes the working electrode 22 to change as the temperature of the circuit changes. For instance, the current through the circuit for a given potential will increase as the temperature of the working electrode 22 increases. Alternatively, the potential required to generate a particular level of current decreases as the temperature of the working electrode 22 increases. Each circuit and solution can be calibrated so as to provide a relationship between the electrical characteristic and the temperature of the working electrode 22. Suitable circuits that include the working electrode 22 include, but are not limited to, a circuit through the working electrode 22, a solution positioned on the sensor 12 and another electrode such as the counter electrode 20 or the reference electrode 18.

During operation of the temperature control system 30, the electronics 38 can monitor one or more electrical characteristics of the circuit. For instance, the electronics 38 can monitor the current, potential and/or the resistance of the circuit. When the one or more electrical characteristics indicates that the temperature of the working electrode 22 has fallen below a first target temperature, the electronics 38 can direct at least a portion of a beam to that sensor. For instance, when the beam distribution system is constructed according to FIG. 2A, the electronics can include the sensor in a scan of the sensor. As another example, when the beam distribution system is constructed according to FIG. 2B, the electronics can move an attenuator out of the path of the beam portion directed to that sensor.

When the one or more electrical characteristics indicate that the temperature of the sensor 12 exceeds a second target temperature, the electronics 38 can reduce the power of the beam directed to the sensor. For instance, when the beam distribution system is constructed according to FIG. 2A, the electronics can remove the sensor from a scan of the sensors. As another example, when the beam distribution system is constructed according to FIG. 2B, the electronics can move an attenuator into the path of the beam portion directed to that sensor.

In some instances, the power of the beam 34 and/or the duration of the beam 34 on a particular sensor 12 can be a function of the difference between the first target temperature and the temperature of the sensor 12 or a function of the difference between the second target temperature and the temperature of the sensor 12. In some instances, the electronics 38 direct the beam 34 to a particular sensor 12 until that sensor 12 exceeds the second target temperature.

The first target temperature can be the same or different from the second target temperature. The first target temperature and the second target temperature can be the same for all of the sensors 12. In some instances, the first target temperature and the second target temperature are different for different sensors 12. As a result, the temperature control system 30 can maintain different sensors 12 at different temperatures.

Although using the electronics to maintain a solution at a target temperature is disclosed in the context of a sensor, the principles can be extended to other solution constraining regions 24. For instance, the electronics can be configured to control the temperature of a solution positioned in a secondary solution constraining region 52 disclosed in FIG. 2C. The secondary solution constraining region 52 can include two spaced apart electrodes that are each positioned so as to contact a fluid constrained in the solution constraining region 24. A circuit that passes a current through the electrodes and the solution can serve as the circuit that is monitored by the electronics. Accordingly, the electronics can adjust the power of the energy beam directed to the secondary solution constraining region 52 in response to one or more electrical characteristics of the circuit. In some instances, one or more of the electrodes included in the circuit also serves as the thermally responsive medium 33 to which the energy beam is directed. Alternatively, the energy beam can be directed to a thermally responsive medium 33 that does not serve as one of the electrodes in the circuit.

Figure 3A:
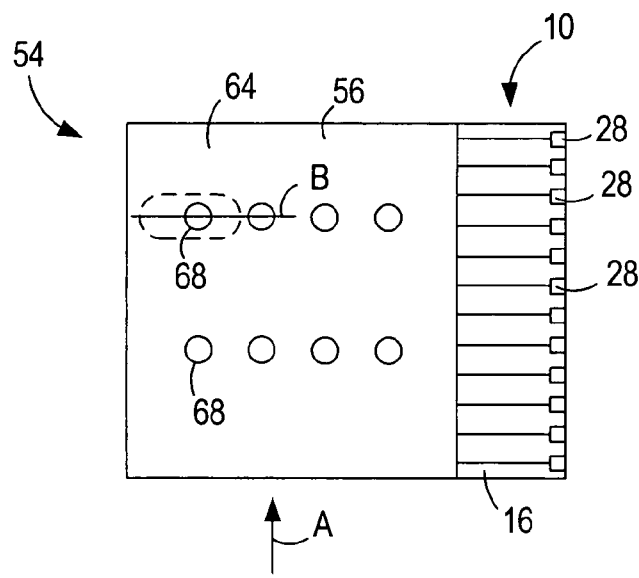
FIG. 3A through FIG. 3C illustrate an assay chip included in a cartridge that can be extracted from a temperature control system.
Figure 3B:
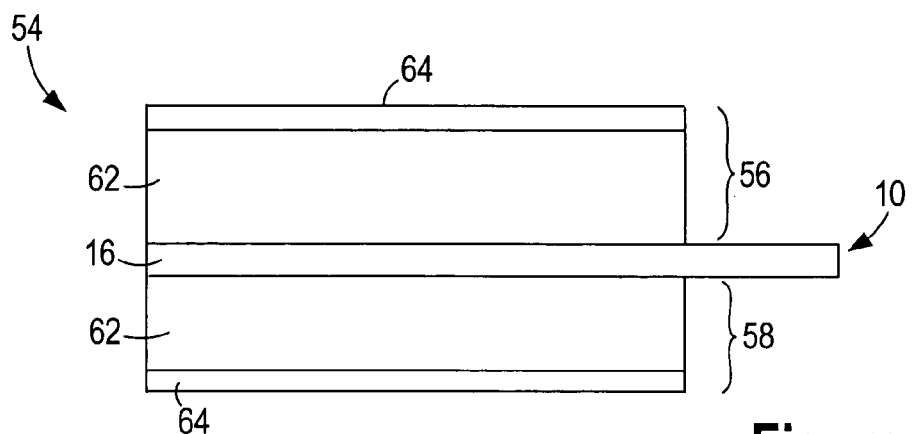

FIG. 3A through FIG. 5B provide an example of an assay system that includes a temperature control system 30. FIG. 3A through FIG. 3C illustrate an assay chip 10 included in a cartridge 54. FIG. 3A is a topview of the cartridge 54. FIG. 3B is a sideview of the cartridge 54 illustrated in FIG. 3A taken in the direction of the line labeled A. FIG. 3C is a cross section of the cartridge 54 illustrated in FIG. 3A taken along the line labeled B.

The cartridge 54 includes a first member 56 and a second member 58 configured to hold the assay chip 10. The first member 56 and the second member 58 each include a base 62 and a cover 64. A suitable material for the first member 56 and the second member 58 includes, but is not limited to, acrylic plastics. Although not shown, pins can extend through the cartridge 54 to keep the various components immobilized relative to one another. For instance, each pin can extend through first member 56, the chip 10 and the second member 58. The use of the pins allows the cartridge 54 components to be separated from one another. The portion of the chip 10 having the pads 28 extends from the cartridge 54. As a result, the chip 10 can be interfaced with a coupler that connects the chip 10 to electronics 38 configured to operate each sensor 12 so as to detect for the presence of an agent.

Figure 3C:
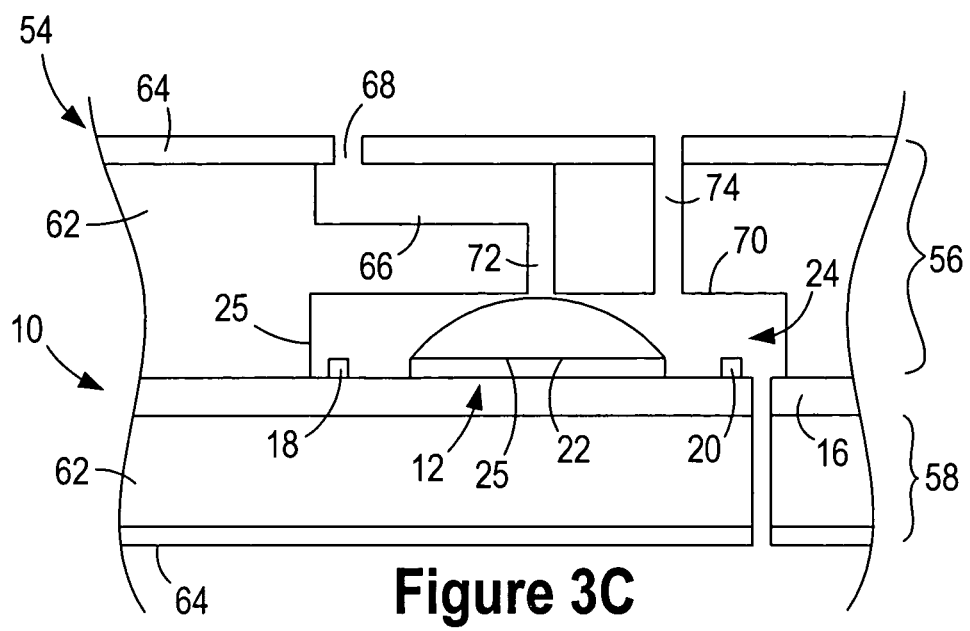

The first member 56 can include one or more reservoirs 66 that each serve as a solution constraining mechanism. Each reservoir 66 is configured to hold a solution to be delivered to one or more sensors 12 located on the chip 10. The cross section shown in FIG. 3C illustrates the relative positions of a reservoir 66 and a sensor 12 positioned on the chip 10. The dashed line in FIG. 2A shows the approximate location of the reservoir 66 within the first member 56. The base 62 of the first member 56 defines a portion of the reservoir 66 and the cover 64 of the first member 56 defines a portion of the reservoir 66. An inlet channel 68 extends through the cover 64 to the reservoir 66.

The sensor 12 is positioned in an assay chamber 70 defined by the chip 10 and the first member 56. An outlet channel 72 extends from the reservoir 66 to the assay chamber 70 through the first member 56. A vent channel 74 extends through the first member 56 to the assay chamber 70. Additionally, a waste channel extends from the assay chamber 70 through the chip 10 and through the second member 58.

During operation of the cartridge 54, a positive pressure is applied to a solution in the reservoir 66. The pressure can be sufficient to transport the solution through the outlet channel 72 into the assay chamber 70 and onto the solution constraining region of the sensor 12. In some instances, the solution fills the entire assay chamber 70 and the assay chambers serves as a solution constraining region. Accordingly, the walls of the assay chamber can serve as a solution constraint mechanism. The positive pressure can be generated by applying increasing the pressure in the inlet channel 68 and/or by sealing the waste channel while decreasing the pressure in the vent channel 74.

Figure 3D:
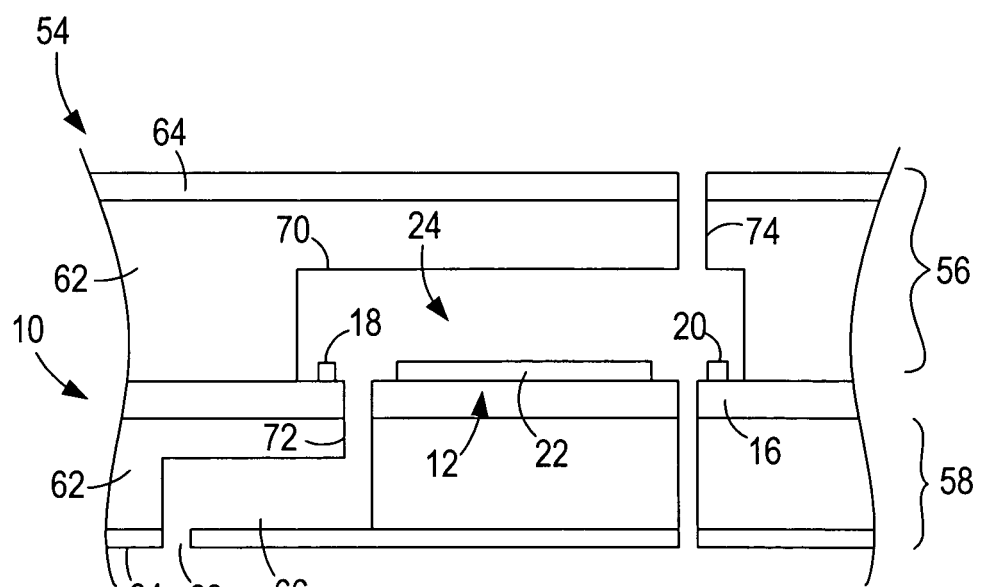
FIG. 3D is a cross section of a cartridge having the reservoir positioned under the assay chip.

The reservoir 66 can be positioned below the chip 10 as shown in FIG. 3D. The base 62 of the second member 58 defines a portion of the reservoir 66 and the cover 64 of the second member 58 defines a portion of the reservoir 66. An inlet channel 68 extends through the cover 64 to the reservoir 66. A sensor 12 is positioned in an assay chamber 70 defined by the chip 10 and the first member 56. An outlet channel 72 extends from the reservoir 66 to the assay chamber 70 through the base 62 of the second member 58 and through the chip 10. During operation of a cartridge 54 constructed according to FIG. 3D, a positive pressure is applied to a solution in the reservoir 66. The pressure is sufficient to transport the solution through the outlet channel 72 into the assay chamber 70 where the solution is formed into a drop on the working electrode.

Figure 3E:
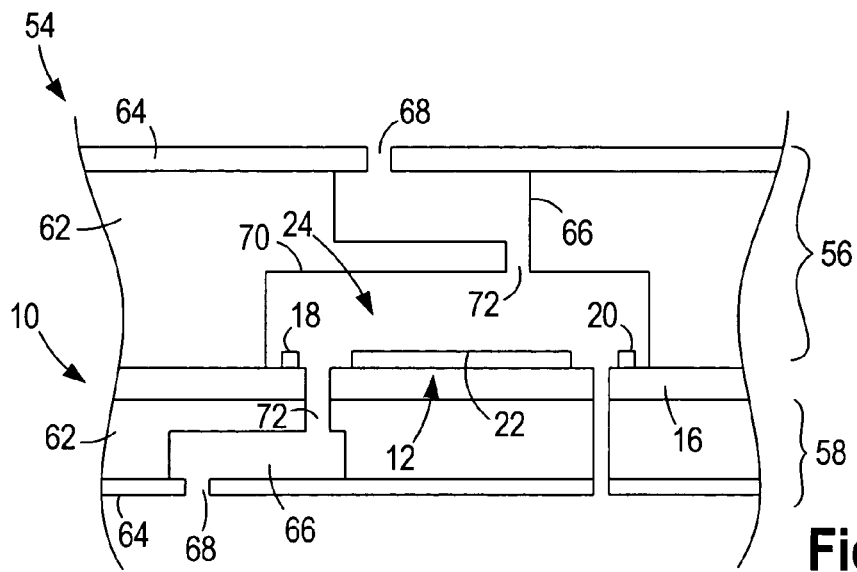
FIG. 3E illustrates a cartridge having a reservoir positioned over a chip having one or more sensors and a reservoir positioned under the chip.

The cartridges 54 illustrated above can be combined to provide a cartridge 54 having a reservoir 66 positioned over the chip 10 and a reservoir 66 positioned under the chip 10 as illustrated in FIG. 3E.

Figure 3F:
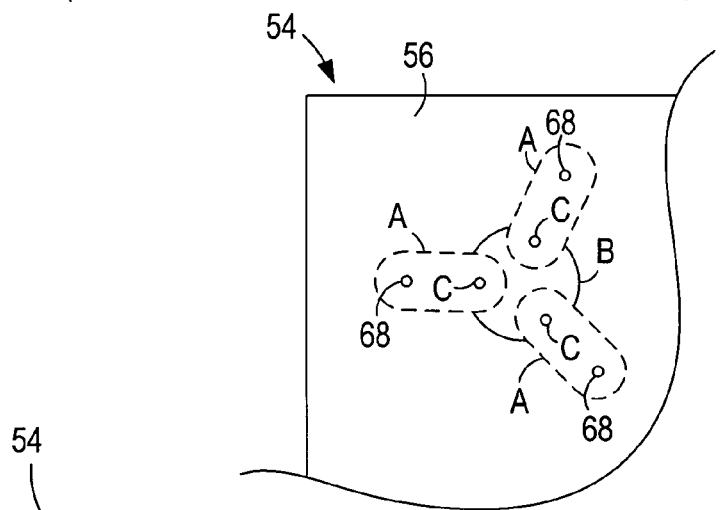
FIG. 3F is a topview of a cartridge having a plurality of reservoirs configured to deliver a solution onto a sensor.

The first member 56 and/or the second member 58 can include a plurality of reservoirs 66 configured to deliver a solution to a sensor 12. For instance, FIG. 3F is a topview of a portion of a cartridge 54. The dashed line labeled B illustrates the location of a working electrode 22 in the cartridge 54. The dashed lines labeled A each illustrate the location of a reservoir 66 configured to deliver a solution onto the working electrode 22. The lines labeled C each illustrate the location of an outlet channel 72 associated with one of the reservoirs 66. Constructing the cartridge 54 such that the first member 56 and/or the second member 58 include a plurality of reservoirs 66 configured to deliver a solution to a sensor 12 can increase the number of solutions that can be delivered onto a single sensor 12.

Figure 3G:
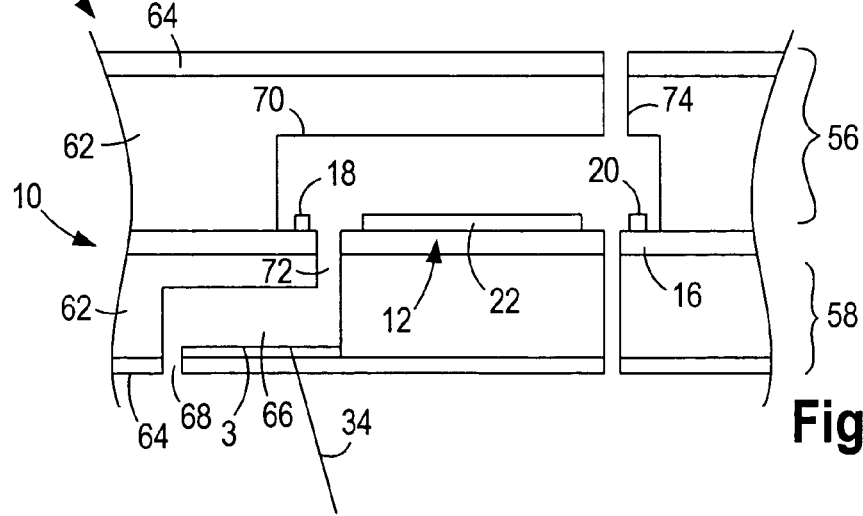
FIG. 3G is a cross section of a cartridge having a reservoir with a thermally responsive medium positioned so as to transfer thermal energy to a solution in the reservoir. An energy beam can be directed to the thermally responsive medium to elevate the temperature of the thermally responsive medium.

As shown in FIG. 3G, the energy beam 34 can be directed to a thermally responsive medium 33 included in the cartridge 54. FIG. 3G is a cross section of a cartridge 54 having a reservoir 66 that includes a thermally responsive medium 33. For instance, all or a portion of the reservoir 66 can include a metal coating that serves as the thermally responsive medium 33. The metal coating can be positioned on the base 62 and/or on the cover 64. When a solution is positioned in the reservoir 66, the temperature control system can be operated so as to direct the energy beam 34 at the thermally responsive medium 33 included in the reservoir 66. Accordingly, the temperature control system can be operated so as to maintain the solution in the reservoir 66 at an elevated temperature. The solution can then be transported from the reservoir 66 to a sensor 12. In some instances, the temperature control system can be operated so as to maintain a solution transported from a reservoir 66 to a sensor 12 at an elevated temperature on the sensor by directing an energy beam 34 to the sensor 12. Alternatively, the temperature control system is not operated so as to maintain the solution transported to a sensor 12 at an elevated temperature after the solution is transported to the sensor 12. In some instances, the electrodes of a sensor 12 may have coatings on them that are sensitive to the energy beam 34. As a result, it is often not desirable to direct the energy beam 34 to the electrodes of the sensor 12. Elevating the temperature of the solution in the reservoir 66 allows the solution to be transported to the sensor 12 at an elevated temperature without the energy beam 34 being directed to the electrodes.

The electronics can be configured to control the temperature of a solution positioned in a reservoir. For instance, the reservoir can be constructed so as to include two electrodes positioned so as to be in contact with a fluid constrained in the reservoir. A circuit that passes a current through the electrodes and the solution can serve as the circuit that is monitored by the electronics. Accordingly, the electronics can adjust the power of the energy beam directed to the reservoir in response to one or more electrical characteristics of the circuit. In some instances, one or more of the electrodes serves as the thermally responsive medium 33 to which the energy beam is directed. Alternatively, the energy beam can be directed to a thermally responsive medium 33 that does not serve as an electrode.

In some instances, the cartridge 54 can be extracted from assay equipment that includes the temperature control system. FIG. 4A through FIG. 4D illustrate an interface system 80 that allows the cartridge 54 to be removably interfaced with assay equipment. FIG. 4A is a topview of an interface system 80 configured to be employed with a cartridge 54 constructed according to FIG. 3A. FIG. 4B is a sideview of the interface system 80 illustrated in FIG. 4A looking in the direction of the arrow labeled A. The interface system 80 includes a first interface member 82 and a second interface member 84. FIG. 4C is a sideview of a cartridge 54 positioned between the first interface member 82 and the second interface member 84 of FIG. 4B. FIG. 4D is a cross section of the interface member seen in FIG. 4A taken along the line labeled B. FIG. 4E is a cross section of the interface member illustrated in FIG. 4A taken between the lines labeled C. The interface member of FIG. 4E is shown coupled with the first member 56 of the cartridge 54 of FIG. 3A.

The cartridge 54 can be interfaced with assay equipment by clamping the cartridge 54 between interface members as shown in FIG. 4C. Accordingly, each interface member is positioned adjacent to a cartridge 54 member when the cartridge 54 is incorporated into the assay equipment. The interface between the first cartridge 54 member and an interface member is shown in FIG. 4E. Suitable materials for construction of the interface members include, but is not limited to, acrylic plastics.

The interface member includes one or more lumens 86 configured to be aligned with the channels 88 on the adjacent cartridge 54 member. The channels 88 with which the lumens 86 are aligned can include inlet channels 68, outlet channels 72, vent channels 74 and waste channels. Each lumen 86 includes a narrow section 90 and d a broad section 92. A connector 94 is inserted into the broad section 92 of the lumen 86. A suitable material for construction of the connector 94 includes, but is not limited to, metals, hard plastics and polymers. The connector 94 includes a flange 96. A sealing mechanism 98 such as an O-ring is positioned between the interface member and the flange 96. The sealing member serves to seal the connection between the connector 94 and the interface member.

The interface member also include a plurality of recesses 100 configured to seat a sealing mechanism 98 around a lumen 86. A suitable sealing mechanism 98 includes, but is not limited to, an O-ring. As is evident in FIG. 4E, the sealing mechanisms 98 seated in the recesses 100 seal the connection between the cartridge 54 member and the interface member.

The connectors 94 can each be coupled with a tube as illustrated in FIG. 4B, and FIG. 4E. Although a single connector 94 is shown as being coupled with a tube, a plurality of the connectors 94 can be coupled with a tube. In some instances, each of the connectors 94 is coupled with a tube. The narrow section 90 of the lumen 86 extends through the connector 94 and the tube. Additionally, the narrow section 90 of the lumen 86 is aligned with a channel 88 through the cartridge 54 member. Accordingly, fluid from the tube can flow from or into the channel 88 in the cartridge 54 member. As a result, the interface system 80 serves to provide fluid communication between the tubes and channels 88 in the cartridge 54. The assay equipment can include valves and/or pumps positioned along each tube for controlling the flow of solutions into and out of the reservoirs 66 in the cartridge 54.

When a member of the cartridge 54 does not include any channels 88, the adjacent interface member need not include any lumens 86. As a result, the adjacent interface member can be a slab.

Figure 5A:
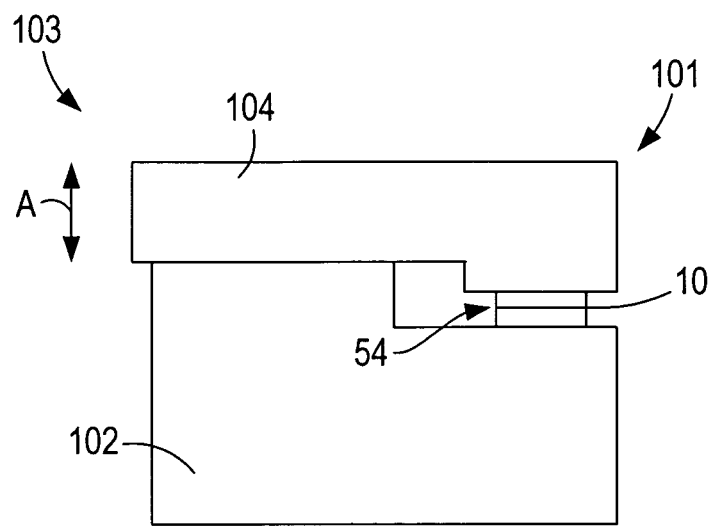
FIG. 5A is a sideview of an assay system for use with a removable cartridge and a temperature control system for elevating the temperature of sensors located in the cartridge.
Figure 5B:
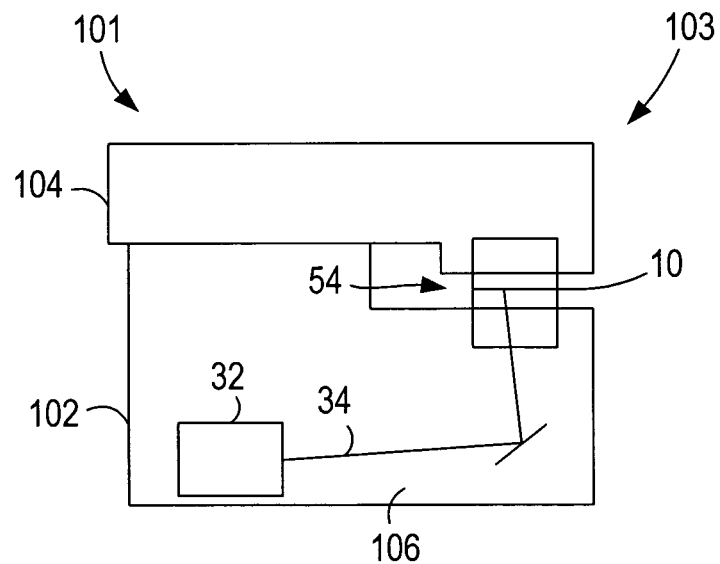
FIG. 5B is a cross sectional view of the assay system shown in FIG. 5A.

FIG. 5A is a sideview of assay equipment 103 for use with a cartridge. FIG. 5B is a cross sectional view of the assay equipment shown in FIG. 5A. The assay equipment 103 can include one or more components for preparing a sample to be assayed, performing the assay and/or analyzing the assay results. The illustrated assay equipment 103 includes a frame 101 with base 102 and an upper body 104. The upper body 104 can be moved relative to the base 102 as illustrated by the arrow labeled A. The base 102 holds the second interface member 84 while the upper body 104 holds the first interface member 82. The cartridge 54 is configured to be coupled with the frame during operation of the assay system and can be removed from the frame. The cartridge 54 can be coupled with the frame by positioning the cartridge 54 on the second interface member 84 and lowering the upper body 104 toward the base 102 until the cartridge 54 is clamped between the first interface member 82 and the second interface member 84 as shown in FIG. 5A. The cartridge 54 can be removed from the frame by moving the upper body 104 away from the base 102 and removing the cartridge 54 from the second interface member 84. When the cartridge is coupled with the frame, the sensors are in electrical communication with the electronics. Although not illustrated, this electrical communication can be achieved by inserting the pads 28 of the chip 10 into a port that provides electrical communication between the sensors and the electronics 36 before or after the cartridge is coupled with the assay equipment 103.

The temperature control system 30 can be positioned in the frame. For instance, the base 102 can include a cavity 106 where the temperature control system is positioned. FIG. 5B illustrates a temperature control system 30 according to FIG. 2A positioned in a cavity 106. The beam source 32 and a steering mirror 37 are positioned in the cavity 106. The cavity 106 is constructed such that a beam 34 from the beam source 32 can travel from the beam source 32 to the steering mirror 37 and from the steering mirror 37 to each of the sensors 12 in the cartridge 54.

As is evident in FIG. 5B, the second interface member 84 is seated in the base 102 such that the beam 34 can be incident on the second interface member 84. The beam 34 passes through the second interface member 84 and through the cartridge 54 before being incident on a sensor 12. The interface members and the cartridge 54 can be constructed of materials that are substantially transparent to the beam 34. For instance, when the beam 34 is a light beam 34, the interface members and cartridge 54 can be constructed from optically transparent media such as acrylic plastics, poly carbonate and PDMS. Alternatively, the interface members and cartridge 54 can be constructed from a medium that is substantially opaque to the energy beam 34. When the interface members and cartridge 54 are opaque, one or more channels can extend through the interface members and cartridge 54 at a location that allows the beam 34 to travel through the channel to the desired location on the sensors 12.

The cartridge 54 embodiment discussed with respect to FIG. 3C or FIG. 3D can be used with the assay system illustrated in FIG. 5A. However, the cartridge 54 embodiment discussed with respect to FIG. 3C has the advantage of having reservoir 66(*s*) positioned over the sensor 12. FIG. 5A illustrates the beam 34 approaching the sensor 12 from the under the sensor 12. As a result, the beam 34 will not have substantial interaction with the reservoirs 66 or their contents. When the embodiment of FIG. 3D is employed, the reservoirs 66 can be arranged so as to reduce interaction with the beam 34.

Although the cavity 106 is shown positioned in the base 102, the cavity 106 can be positioned in the upper body 104. As a result, in some instances, the beam 34 approaches the sensors 12 from the over the sensor 12. The cartridge 54 embodiment discussed with respect to FIG. 3C or FIG. 3D can be used with an assay system arranged such that the beam 34 approaches from over the sensors 12. However, the cartridge 54 embodiment discussed with respect to FIG. 3D has the advantage of having reservoir 66(*s*) positioned under the sensor 12. As a result, the beam 34 will not have substantial interaction with the reservoirs 66 or their contents when the embodiment of FIG. 3D is employed. When the embodiment of FIG. 3C is employed, the reservoirs 66 can be arranged so as to reduce interaction with the beam 34.

In many instances, interaction of the beam 34 and the reservoirs 66 and/or their contents does not affect performance of the assay or of the temperature control system 30. In these instances, the choice of cartridges 54 does not necessarily provide an advantage.

The assay equipment is illustrated as including the temperature control system, however, the assay equipment can include a variety of other components. Examples of components that can be included in the assay equipment 103 include, but are not limited to, the interface system 80, the beam distribution system 36, electronics 38, tubes, valves and pumps Examples of components that can be included in the assay equipment 103 include, but are not limited to, the interface system 80, the temperature control system 30, the beam distribution system 36, pumps, valves, electronics 38. The various components can be included in the frame or can be positioned in a variety of different locations.

The sensors 12 illustrated above are for illustrative purposes only and the temperature control system 30 can be employed in conjunction with other types of sensors 12 configured to detect agents.

Although the assay system is disclosed in the context of a particular sensor embodiment, the assay system can be employed in conjunction with other sensor types and constructions. Further, the sensor need not be limited to detection of biological agents and can be a sensor for the detection of other agents such as chemicals and particulates, electrolytes and molecules.

Additionally, the cartridge 54 and interface systems 80 shown are provided to illustrate an interface between an assay chip 10 and an assay system. As a result, the temperature control system 30 can be employed in conjunction with other arrangements. For instance, some assay systems may not include a cartridge 54 or an interface system 80. Further, some assay systems may not include a cartridge 54 and or interface system 80 that is removable from the assay system.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. An assay system, comprising:
one or more electrochemical sensors that each includes an electrode, each of the one or more sensors being positioned on a common substrate, and each of the sensors being configured to detect an agent in a liquid;
an energy beam source configured to produce an energy beam; and
a beam distribution system configured to distribute the energy beam to the one or more sensors such that the energy beam interacts with the electrode in each of the sensors so as to elevate the temperature of each of the one or more sensors.

2. The assay system of claim 1, wherein the energy beam is a light beam.

3. The assay system of claim 1, wherein the beam distribution system is configured to direct the energy beam at a working electrode in each of the one or more sensors so as to elevate the temperature of the working electrode.

4. The assay system of claim 1, wherein the one or more sensors is a plurality of sensors and the beam distribution system is configured to direct the energy beam from one of the sensors to another sensor.

5. The assay system of claim 4, wherein the beam distribution system includes an electronically steered mirror.

6. The assay system of claim 1, further comprising:
one or more lenses positioned along a path of the energy beam and configured to adjust a spot size of the energy beam on the one or more sensors.

7. The assay system of claim 1, further comprising:
an attenuator configured to at least partially attenuate the power of the energy beam.

8. The assay system of claim 7, wherein the attenuator is configured to be moved in and out of a path of the energy beam.

9. The assay system of claim 7, wherein the attenuator is configured to provide complete blocking of the energy beam.

10. The assay system of claim 1, wherein the beam distribution system is configured to split the energy beam into a plurality of energy beam portions that are each directed to a sensor.

11. The assay system of claim 10, further comprising:
a plurality of attenuators each configured to at least partially attenuate the power of an energy beam portion.

12. The assay system of claim 10, wherein at least one attenuator is configured to provide complete blocking of an energy beam portion.

13. The assay system of claim 10, further comprising:
electronics configured to monitor one or more electrical characteristics of a circuit that includes an electrode associated with at least one of the one or more sensors, the one or more monitored electrical characteristics indicating a temperature of the sensor.

14. The assay system of claim 13, wherein the electronics are configured to operate the beam distribution system such that at least a portion of the energy beam is distributed to the sensor in response to the one or more electrical characteristics indicating that the temperature of the associated sensor falls below a first target temperature.

15. The assay system of claim 14, wherein the electronics are configured to operate the beam distribution system such that distribution of the energy beam to the associated sensor is disrupted in response to the one or more electrical characteristics indicating that the temperature of the associated sensor is elevated above a second target temperature.

16. The assay system of claim 1, wherein the one or more sensors are included in a cartridge that is removable from the assay system.

17. The assay system of claim 1, wherein the one or more sensors are included in a cartridge.

18. The assay system of claim 17, wherein the one or more sensors are included on an assay chip.

19. The assay system of claim 17, wherein each of the one or more sensors includes a working electrode.

20. The assay system of claim 1, wherein the one or more electrochemical sensors is multiple electrochemical sensors, each of the electrochemical sensors includes a working electrode and the beam distribution system includes an electronically steered mirror configured to steer the energy beam from one of the working electrodes to another working electrode.

21. The assay system of claim 20, wherein the beam distribution system is configured to split the energy beam into a plurality of energy beam portions that are each directed to one of the working electrodes.

22. The assay system of claim 1, wherein the energy beam travels through the substrate before coming into contact with the electrode.

23. The assay system of claim 22, wherein the sensor is configured to receive the liquid such that the electrode is between the liquid and the substrate.

24. The assay system of claim 1, wherein the one or more sensors is a plurality of sensors and the energy beam travels through the substrate before coming into contact with the electrode included in each of the sensors.

25. The assay system of claim 24, wherein each of the sensors are configured to receive the liquid such that the electrode is between the liquid and the substrate.

26. The assay system of claim 1, wherein each of the sensors includes electrodes and the electrodes from different sensors are positioned on a common substrate and the beam distribution system is configured such that when the energy beam is directed to each of the sensors, the energy beam travels through the substrate before coming into contact with one of the electrodes included in the sensor.

27. The assay system of claim 1, further comprising:
electronics configured to raise a potential difference between electrodes included in each of the one or more electrochemical sensors to a level where electron transfer occurs between one of the electrodes and a component in a sample positioned on each of the one or more electrochemical sensors.

28. The assay system of claim 1, wherein each of the one or more electrochemical sensors includes a working electrode, a counter electrode, and a reference electrode and further comprising: electronics configured to raise a potential applied between the working electrode and the reference electrode to a level that causes electron transfer to occur between the working electrode and a component in a sample positioned on each of the one or more electrochemical sensors, the electron transfer allowing current to flow through a circuit that includes the working electrode, the sample and the counter electrode.

\* \* \* \* \*